United States Patent [19]

Daniel

[11] Patent Number: 5,000,176
[45] Date of Patent: Mar. 19, 1991

[54] THERAPEUTIC WRAP

[76] Inventor: Mary K. Daniel, 2204 Patricia La., Boise, Id. 83704

[21] Appl. No.: 413,706

[22] Filed: Sep. 28, 1989

[51] Int. Cl.$^5$ .............................................. A61F 7/02
[52] U.S. Cl. .................................... 128/402; 128/384
[58] Field of Search ............... 128/402, 403, 379, 380, 128/384; 62/530

[56] References Cited

U.S. PATENT DOCUMENTS

| | | | |
|---|---|---|---|
| 2,715,315 | 8/1955 | Giardini | 128/380 |
| 3,175,558 | 3/1965 | Cailouette et al. | 128/403 |
| 3,889,684 | 6/1975 | Lebold | 128/402 |
| 4,055,188 | 10/1977 | Pelton | 128/402 |
| 4,585,003 | 4/1986 | Meistrell | 128/402 |
| 4,676,247 | 6/1987 | Van Cleve | 128/402 |
| 4,688,572 | 8/1987 | Hubbard et al. | 62/530 |

Primary Examiner—Edward M. Coven
Assistant Examiner—Mark S. Graham
Attorney, Agent, or Firm—Paul F. Horton

[57] ABSTRACT

A therapeutic wrap for holding a heat transference device, such as an ice pack or a hot pack, in contact with the human body. The wrap includes a first elongated flap, upon which the pack is placed, and three additional flaps, foldable over the pack, to define a closed pocket for retention of the pack. The first flap is of sufficient length so as to encircle a body part, such as an arm, thigh, or waist. Fasteners, preferably of the hook-loop type, insure the integrity of the pocket and provide for securement of the wrap around the body. A modified embodiment of the wrap includes a first elongated flap and only two additional flaps to define an open pocket for use about the waist or thorax. The wrap is preferably constructed of a single sheet of material.

4 Claims, 1 Drawing Sheet

U.S. Patent  Mar. 19, 1991  Sheet 1 of 1  5,000,176
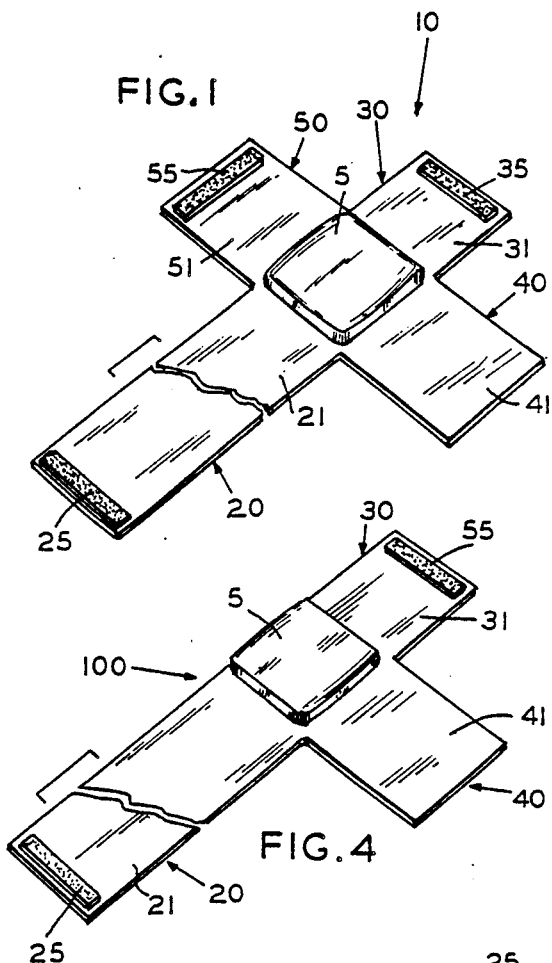
FIG. 1
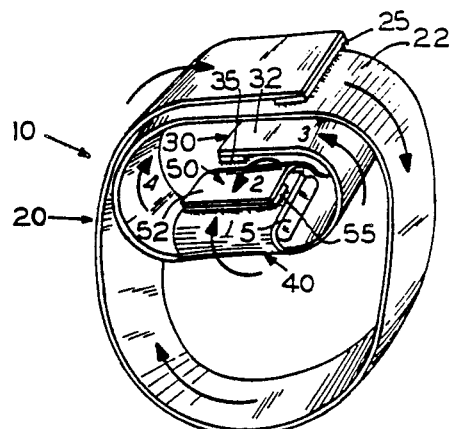
FIG. 2
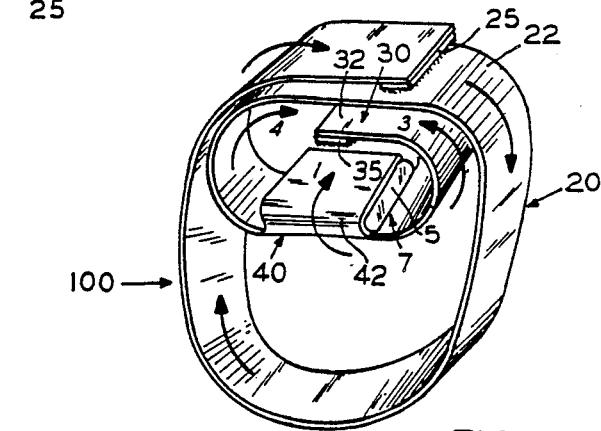
FIG. 4
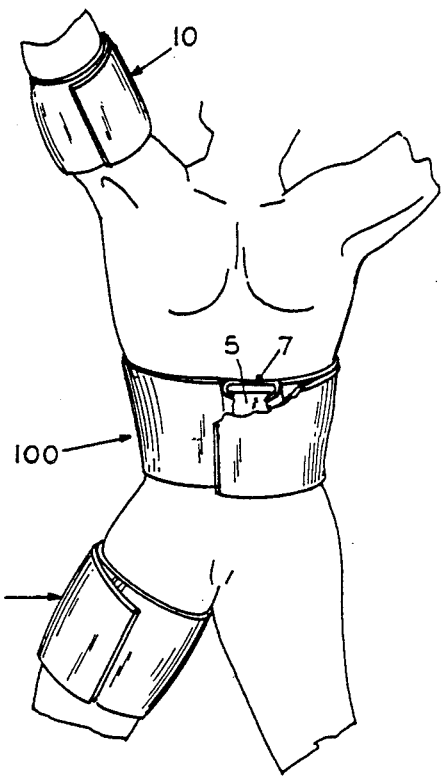
FIG. 3
FIG. 5

THERAPEUTIC WRAP

BACKGROUND OF THE INVENTION

1. Field of the Invention

This invention relates, in general, to therapeutic wraps and, more particularly, to therapeutic wraps for holding heat transference hot and cold packs against a body portion of the user.

2. Description of the Prior Art

The convenience of a wrap for holding a hot or cold pack or compress against the body has long been recognized. Such wraps enable the individual to enjoy the benefits of the pack without the bother of manually holding the pack in place.

Early wraps simply held the pack against the body part without the aid of pockets or pouches, and therefore the pack often slipped from the wrap.

Conventional wraps, as typified by U.S. Pat. Nos. 4,527,566, issued to H. Abare; 4,556,055, issued to F. Bonner, Jr.; 4,592,358, issued to W. Westplate; and 4,676,247, issued to A. Van Cleve, are all provided with pockets of set size, which are stitched or otherwise crafted into the wrap. Such pockets make inspection difficult; limit the size of hot-cold packs which may be used; and present cleaning and laundering problems. Other wraps, such as the wrap disclosed by S. Lebold, U.S. Pat. No. 3,889,684, utilize mating Velcro ® strips to hold the packs in place, which simply the inspection and cleaning problems. The Lebold wrap, in having a boundary of mating Velcro ® strips, has a pocket limited in size and also, undesirably, permit packs of smaller size to slip around within the pocket in that the packs are not secured to the pocket. Construction expense, is increased by the use of separate sheets of material defining the pocket and numerous straps for attaching the wrap to the body.

SUMMARY OF THE INVENTION

The present invention comprises, generally, a therapeutic wrap for holding hot or cold packs. The wrap is cut of a single sheet of material to define an elongated flap for encircling a body part and two or three additional flaps which, when folded, define a pocket of precise size for the retention of the pack. Velcro ® fasteners are used to hold the flaps in place. A more thorough description of the invention may be found in the appended claims.

It is therefore a primary object of the present invention to provide a therapeutic wrap for hot and cold packs which is constructed of a single piece of sheet material for cost efficiency; convenience of inspection; convenience of laundering; and convenience of use.

It is another object of the present invention to provide a therapeutic wrap for hot and cold packs which includes foldable flaps, with fasteners, for defining retention pockets of varying size and yet pockets which have dimensions closely approximating the packs for securely holding the packs without slippage.

It is also an object of the present invention to provide a therapeutic wrap for hot and cold packs which is easily applied to the body part; which is readily adjustable to the size of the body part; and with which hot or cold packs can readily be replaced.

Additional objects and advantages will become apparent and a more thorough and comprehensive understanding may be had from the following description take in conjunction with the accompanying drawings forming a part of this specification.

BRIEF DESCRIPTION OF THE DRAWINGS

FIG. 1 is a perspective view of a preferred embodiment of the wrap of the present invention, showing the heat transference pack in place.

FIG. 2 is a perspective view of the wrap of the present invention showing the folded position of the flaps to define a closed pocket.

FIG. 3 is a schematic showing the wraps of the present invention attached to various body parts.

FIG. 4 is a perspective view of a second preferred embodiment of the wrap of the present invention, showing placement of a heat transference pack.

FIG. 5 is a perspective view of the second embodiment of the wrap showing the folded position of the flaps to define an open pocket.

DETAILED DESCRIPTION OF THE INVENTION

Referring now to FIGS. 1 and 2, in particular, an embodiment to be preferred of a therapeutic wrap 10, made according to the present invention is disclosed. Wrap 10 includes a first elongated flap 20; a second flap 30; a third flap 40; and a fourth flap 50. Each of the flaps are preferably integral with one another and the wrap may be manufactured from a single sheet of cloth fabric, cut into the shape of a cross-like structure, to define the flaps. The fabric may include a multiplicity of loops for engagement with fasteners provided with a multiplicity of hooks, as will hereinafter be explained.

First flap 20 may be of any suitable length and width; it being only necessary that the flap be of sufficient length to encircle the body part being treated. The first flap, on its top surface 21, at the center of the cross-like structure and adjacent the other flaps, includes an area for placement of a heat transference device 5, which may be a hot or cold pack or bag. The width of the first flap should be approximately the same as the width of the pack. The second flap 30 is a short flap, having a length suitable for folding over heat transference device 5, as shown in FIG. 2. The width of flap 30 is preferably the same as the first flap. The second flap is in alignment with the first flap and is, effectively, an extension of the first flap, being defined by its border with the laterally extending flaps. Third flap 40 extends laterally from the first flap and second flap a sufficient length to fold over device 5 at right angles relative to the second flap, as shown in FIG. 2. Fourth flap 50 extends laterally from the first flap in a direction opposite from and in alignment with the third flap. The fourth flap is of sufficient length to fold over device 5, also at right angles to the second flap, as shown in FIG. 2.

On top surface 21 and adjacent the terminal free end of first flap 20 is first flap fastening means 25, including a strip of material having a multiplicity of hooks and sold under the trademark Velcro ®. Likewise, second flap 30 and either third flap 40 or fourth flap 50 are provided with fastening means 35 and 55 on their top surfaces. Fastening means 35 and 55 also utilize a Velcro ® strip adjacent their free terminal ends.

Referring now to FIGS. 2 and 3, taken in conjunction with FIG. 1, use of therapeutic wrap 10 is shown. Assuming the wrap is to be used for placing a heat transference device 5, such as a hot pack, on the thigh of the individual, the hot pack is first placed on the top surface of the wrap in the position shown in FIG. 1. Next, either flap 40 or 50 is folded over the top of the pack, depending upon which flap is provided with a fastener. In the embodiment shown, third flap 40 is first folded over the pack, as shown by arrow 1 in FIG. 2, enclosing one side of the pack, and then fourth flap 50 is folded over the pack, as shown by arrow 2, enclosing the opposing side of the pack and Velcro ® strip 55, on the top surface of the fourth flap, is caused to engage the loops of the material on the bottom surface 42 of third flap 40. Next, second flap 30 is folded over the pack, as shown by arrow 3, and is fastened to the bottom surface 52 by means of fastener 35, to enclose one end of the pack. It is to be appreciated that, in this manner, varying sizes of packs may be enclosed and that the pocket defined by the overlapping flaps is precisely the size of the pack. Elongated first flap 20 is then folded over the top of the pack and over second flap 30, as shown by arrow 4, to enclose the other end of the pack and to define a closed pocket from which the pack cannot be accidently removed. The first flap is then brought around the body part, such as the thigh, causing the flap to encircle the thigh and is fastened to bottom surface 22 of itself by means of fastener 25, the hooks of the fastener engaging the loops of the material. In this manner, the wrap can be secured to body parts of varying circumferences; the axis of the body part being designated by the broken line in FIG. 2.

Referring now to FIGS. 4 and 5, a modified embodiment 100 of the therapeutic wrap is shown. Embodiment 100 is identical to wrap 10, except for the omission of one of the lateral flaps, and therefore the same numbers are used to identify the same parts as in the first embodiment. Wrap 100 is used in the same manner as the first embodiment, but the omission of one of the lateral flaps causes an "open" pocket to be defined by the flaps, as shown in FIG. 5. This wrap is therefore to be used only where the pocket opening, designated by the numeral 7, is up, such as is shown in FIG. 3, where the wrap is used around the waist or thorax. In this position, the hot or cold pack 5 may be removed an replaced without undoing the wrap.

Having thus described in detail a preferred selection of embodiments of the present invention, it is to be appreciated and will be apparent to those skilled in the art that many physical changes could be made in the apparatus without altering the inventive concepts and principles embodied therein. The present embodiments are therefore to be considered in all respects as illustrative and not restrictive, the scope of the invention being indicated by the appended claims rather than by the foregoing description, and all changes which come within the meaning and range of equivalency of the claims are therefore to be embraced therein.

I claim:

1. Therapeutic wrap for holding a heat transference device into heat transferring contact with a body part, said wrap comprising:
    a heat transference device;
    a first elongated flap having a top surface suitable for placement of the heat transference device thereon, and the remainder of said flap operable to encircle the body part;
    a second flap in alignment with said first flap for folding over the heat transference device to engage one side thereof;
    a third flap laterally extending from said first flap for folding over the heat transference device to engage a second side thereof;
    a fourth flap laterally extending from said first flap and in alignment with said third flap for folding over the heat transference device to engage a third side thereof; and
    first flap fastening means for affixing said first flap to itself upon encirclement of the body part; said flaps engaging one another to define a closed pocket for retention of the heat transference device, said wrap comprising a cross-shaped sheet of fabric material.

2. The wrap as described in claim 1 wherein said first flap is constructed of a first fabric and said fastening means is constructed of a second fabric operable to engage said first fabric in a hook-loop relationship.

3. The wrap as described in claim 1 further comprising at least one additional fastening means for affixing said flaps to one another adjacent said pocket.

4. Therapeutic wrap for holding a heat transference device into heat transferring contact with a body part, said wrap comprising:
    a heat transference device;
    a first elongated flap having a top surface suitable for placement of the heat transference device thereon, and the remainder of said flap operable to encircle the body part;
    a second flap in alignment with said first flap for folding over the heat transference device to engage one side thereof;
    a third flap laterally extending from said first flap for folding over the heat transference device to engage a second side thereof;
    a fourth flap laterally extending from said first flap and in alignment with said third flap for folding over the heat transference device to engage a third side thereof; each of said flaps unitary with one another and constructed of a fabric provided with a multiplicity of loops;
    first fastening means affixed to said first flap and said fastening means provided with a multiplicity of hooks for engaging said first flap to itself upon encirclement of a body part;
    second fastening means affixed to said second flap for fastening said second flap to an underlying flap over the heat transference device; and
    third fastening means affixed to said third or fourth flap for fastening said flap to an underlying flap over the heat transference device; said flaps engaging one another to define a closed pocket for retention of the heat transference device.

* * * * *